(12) United States Patent
Mistry et al.

(10) Patent No.: US 7,235,646 B2
(45) Date of Patent: Jun. 26, 2007

(54) PROCESS FOR THE PREPARATION OF AZITHROMYCIN MONOHYDRATE ISOPROPANOL CLATHRATE

(75) Inventors: Dhiren Natavarlal Mistry, Gujarat (IN); Mahadeo Maroti Thorat, Gujarat (IN); Kamlesh Sanmukhubhia Soni, Gujarat (IN); Vinod Kumar Kansal, Gujarat (IN)

(73) Assignee: Alembic Limited, Vadodara, Gujarat (IN)

( * ) Notice: Subject to any disclaimer, the term of this patent is extended or adjusted under 35 U.S.C. 154(b) by 31 days.

(21) Appl. No.: 11/166,250

(22) Filed: Jun. 27, 2005

(65) Prior Publication Data

US 2006/0019908 A1 Jan. 26, 2006

(30) Foreign Application Priority Data

Jun. 28, 2004 (IN) ........................ 687/MUM/2004

(51) Int. Cl.
*C07H 17/08* (2006.01)
(52) U.S. Cl. ...................................... 536/7.4; 536/18.5
(58) Field of Classification Search ................ 536/7.4, 536/18.5
See application file for complete search history.

(56) References Cited

U.S. PATENT DOCUMENTS 4,517,359 A * 5/1985 Kobrehel et al. ............ 536/7.4
6,245,903 B1 * 6/2001 Karimian et al. ............ 536/7.4
6,268,486 B1 7/2001 Kunikata et al.

FOREIGN PATENT DOCUMENTS

EP 0 298 650 A2 1/1989
WO WO 94/26758 A1 11/1994

OTHER PUBLICATIONS

Dunn et al., "Azithromycin, A Review of its Pharmacological Properties and Use as 3-day Therapy in Respiratory Tract Infections", *Drugs* Mar. 1996 pp. 483-505.

* cited by examiner

*Primary Examiner*—Elli Peselev
(74) *Attorney, Agent, or Firm*—Westerman, Hattori, Daniels & Adrian, LLP.

(57) ABSTRACT

The present invention relates to an improved, cost effective and easy process for the preparation of azithromycin monohydrate isopropanol clathrate. The process provides a one-step method of preparing azithromycin monohydrate isopropanol clathrate directly from 9-deoxo-9a-aza-9a-homoerythromycin A. The process comprises at least partial dissolution and/or suspension of 9-deoxo-9a-aza-9a homo-erythromycin A in isopropanol to form a mixture, adding methylating solution to the said mixture, refluxing or heating said mixture to form a reaction mixture, adding alkaline solution to the reaction mixture to adjust pH from about 10 to about 11 and isolating pure azithromycin monohydrate isopropanol clathrate. The process helps in reducing the total time of preparation, total utility cost for the production and also helps to avoid handling loss.

11 Claims, 2 Drawing Sheets

PROCESS FOR THE PREPARATION OF AZITHROMYCIN MONOHYDRATE ISOPROPANOL CLATHRATE

FIELD OF THE INVENTION

The present invention relates to an improved, cost effective and easy process for the preparation of azithromycin monohydrate isopropanol clathrate. In particular, the present invention relates to a process for the preparation of azithromycin monohydrate isopropanol clathrate directly from 9-deoxo-9a-aza-9a-homoerythromycin A (herein after referred to as azaerythromycin).

BACKGROUND OF THE INVENTION

Azithromycin, 9-Deoxo-9a-aza-9a-methyl-9a-homoerythromycin A, is a 15 member ring macrolide belonging to a new class of antibiotics termed "Azalides", due to the incorporation of a nitrogen atom in the macrocyclic ring.

Azithromycin (Formula I) is derived from the 14-membered macrolide antibiotic erythromycin A and shows significant improvement in its activity against gram—Ve organisms compared to erythromycin A (C. J. Dunn and L. B. Barradell Azithromycin: A Review of its Pharmacological properties and use as a 3-day therapy in respiratory tract infections, Drug, 1996, March, 51(3) 483–505).

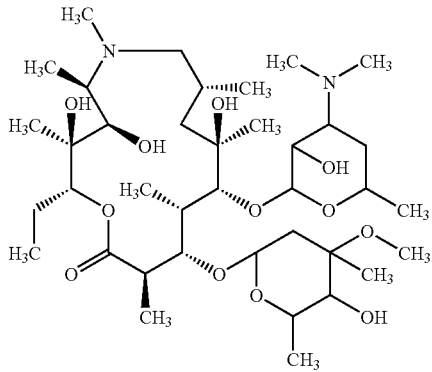

Formula I

Azithromycin was first discovered by G. Kobrehel and S. Djokic (U.S. Pat. No. 4,517,359; S. Djokic et al.). U.S. Pat. No. 4,517,359 describes methylation of 11-aza-10-deoxo-10-dihydro erythromycin A (presently called 9-Deoxo-9a-aza-9a-homoerythromycin A) in an excess of formaldehyde and formic acid in a halogenated hydrocarbon, e.g., chloroform or carbon tetrachloride. In the procedure described in U.S. Pat. No. 4,517,359 the isolation of azithromycin comprises extraction of the aqueous layer with a halogenated hydrocarbon solvent followed by evaporation of the solvent. The disadvantages of this process are that (i) a halogenated hydrocarbon is used which is environmentally unsafe and (ii) the isolation of azithromycin involves several cumbersome and/or inefficient extraction and solvent evaporation steps. According to European Patent Application EP 298650, the azithromycin obtained by the process taught in U.S. Pat. No. 4,517,359, is a hygroscopic monohydrate. Because of its hygroscopic nature, this monohydrate is difficult to prepare and maintain in a form having a constant, reproducible water-content, and is particularly difficult to handle during formulation.

The processes taught in U.S. Pat. No. 6,268,489 for the preparation of azithromycin dihydrate, while producing a non-hygroscopic form of azithromycin, have a number of disadvantages:
1. Water immiscibility of the organic solvent mixture (tetrahydrofuran plus hexane) can cause problems in obtaining pure material since crystallization processes are known to afford pure material when the anti-solvent is miscible with the solvent used to dissolve the crude product.
2. The drying process must be very carefully controlled since an increase in temperature will cause the transformation of the non-hygroscopic dihydrate to the hygroscopic monohydrate.
3. The use of low boiling point solvents is complicated by their toxicity and possibility of formation of explosive peroxide during solvent recovery.

Two other synthesis routes, affording azithromycin as a form that should differ from the crystalline ones previously mentioned, have also been described in WO 94/26758 and U.S. Pat. No. 4,517,359. According to such processes azithromycin is obtained by single evaporation to dryness. However, in these prior art documents there is no reference to the crystalline state of the azithromycin thus obtained.

Azihthromycin monohydrate isopropanol clathrate is taught in U.S. Pat. No. 6,245,903. According to this processes the azithromycin monohydrate isopropanol clathrate is obtained from azithromycin, azithromycin monohydrate or azithromycin dihydrate. There are two steps involved in this process, first step is isolating azithromycin in any form (i.e. azithromycin monohydrate or azithromycin dihydrate) from azaerythromycin and second step is the conversion of azithromycin to azithromycin monohydrate isopropanol clathrate.

Being of two steps, the process of U.S. Pat. No. 6,245,903 has the following drawbacks.
1) Substantial total time of process
2) High total utility cost of production
3) Loss of materials during handling.

OBJECTS OF THE INVENTION

Therefore the basic object of the present invention is to provide a one-step process for manufacturing pure azithromycin clathrate.

Another object of the present invention is to provide a process for manufacturing pure azithromycin clathrate which is cost-effective.

A further object of the present invention is to provide direct isolation of azithromycin monohydrate isopropanol clathrate from azaerythromycin.

A further object of the present invention is to provide azithromycin monohydrate isopropanol clathrate, which is crystalline and, in contrast to anhydrous azithromycin, is obtained in pure form.

Another object of the present invention is to provide azithromycin monohydrate isopropanol clathrate, which is not hygroscopic.

Another object of the present invention is to provide azithromycin monohydrate isopropanol clathrate in higher yield.

Another object of the present invention is to provide azithromycin monohydrate isopropanol clathrate, which is reproducible in a wide spectrum of physical conditions and consistently afford azithromycin monohydrate isopropanol clathrate with a constant ratio of azithromycin, water and isopropanol (vacuum drying at 1–10 mm Hg at 25 to 60.degree. C. for 2 to 12 hours).

Yet another object of the present invention is to provide azithromycin monohydrate isopropanol clathrate, which is in high yields of the product within the range of 91% to 98% (first crop) and it is directly isolated from the azaerythromycin.

Yet further object of the present invention is to provide azithromycin monohydrate isopropanol clathrate, which is very economical and pure (HPLC Purity 97–99%).

SUMMARY OF THE INVENTION

Thus according to the present invention, the invention relates to a process for the preparation of azithromycin monohydrate isopropanol clathrate directly from azaerythromycin

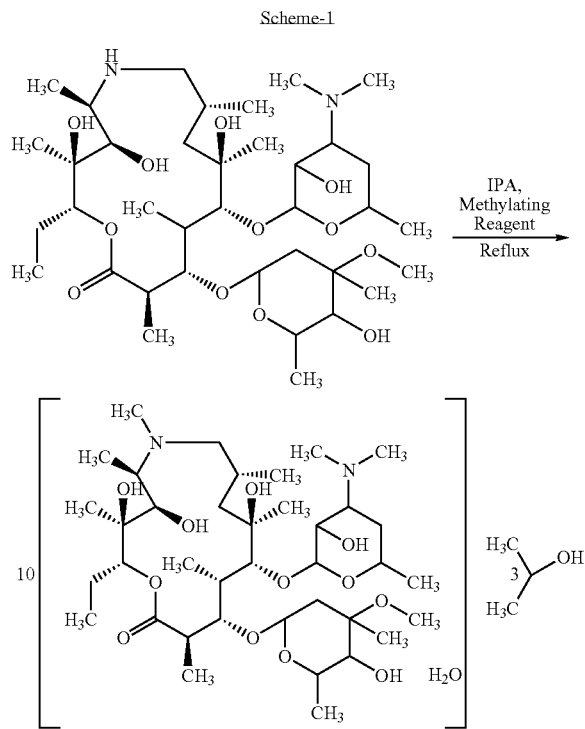

Scheme-1 comprising the steps of:
a) at least partial dissolution and/or suspension of 9-deoxo-9a-aza-9a homoerythromycin A in isopropanol to form a mixture;
b) adding methylating solution to the said mixture;
c) refluxing or heating said mixture to form a reaction mixture;
d) adding alkaline solution to the reaction mixture to adjust pH from about 10 to about 11;
e) isolating pure azithromycin monohydrate isopropanol clathrate.

The step of isolating pure azithromycin monohydrate isopropanol clathrate comprises the steps of:
(a) separating the organic layer from said reaction mixture;
(b) adding water to said reaction mixture to precipitate said azithromycin monohydrate isopropanol clathrate;
(c) filtering out said azithromycin monohydrate isopropanol clathrate;
(d) vacuum drying the said azithromycin monohydrate isopropanol clathrate.

The methylating reagent is selected from formaldehyde, formic acid, paraformaldehyde and mixture thereof.

The alkaline solution is selected from the group consisting of sodium hydroxide solution, potassium hydroxide solution preferably sodium hydroxide solution.

BRIEF DESCRIPTION OF THE ACCOMPANYING DRAWINGS

DETAILED DESCRIPTION OF THE INVENTION

The present invention describes a process for the preparation of pure azithromycin monohydrate isopropanol clathrate.

One molecule of azithromycin monohydrate isopropanol clathrate consists of three molecules of isopropanol for every ten molecules of azithromycin monohydrate.

The process comprises n-methylation of azaerythromycin in isopropanol in presence of methylating agent and the reaction is stopped by aqueous base. The organic layer is separated and cooled slowly, resulting in the precipitation of azithromycin monohydrate isopropanol clathrate by addition of water.

The volume of solvent used is such as to be sufficient to suspension or dissolution of azaerythromycin. The suspension temperature is between ambient to reflux temperature of solvent. An amount of water, which is necessary for the formation of azithromycin solvate in the form of a monohydrate, may be present in the organic solvent.

The mixture is stirred for 2 to 24 hrs and the reaction temperature is from room temperature to the reflux temp of solvent. The product is filtered and washed with isopropanol: water mixture and dried under vacuum (1–10 mm Hg) at 25–90° C. for 2–24 hours to obtain azithromycin monohydrate isopropanol clathrate in high yields. Extension of vacuum drying does not reduce either the water content or the isopropanol content of azithromycin monohydrate isopropanol clathrate.

Elemental analysis, 1HNMR, 13C NMR, and IR spectroscopy, mass spectrometry, and power x-ray diffraction and IR have identified the azithromycin monohydrate isopropanol clathrate produced according to the invention.

Figure 1:
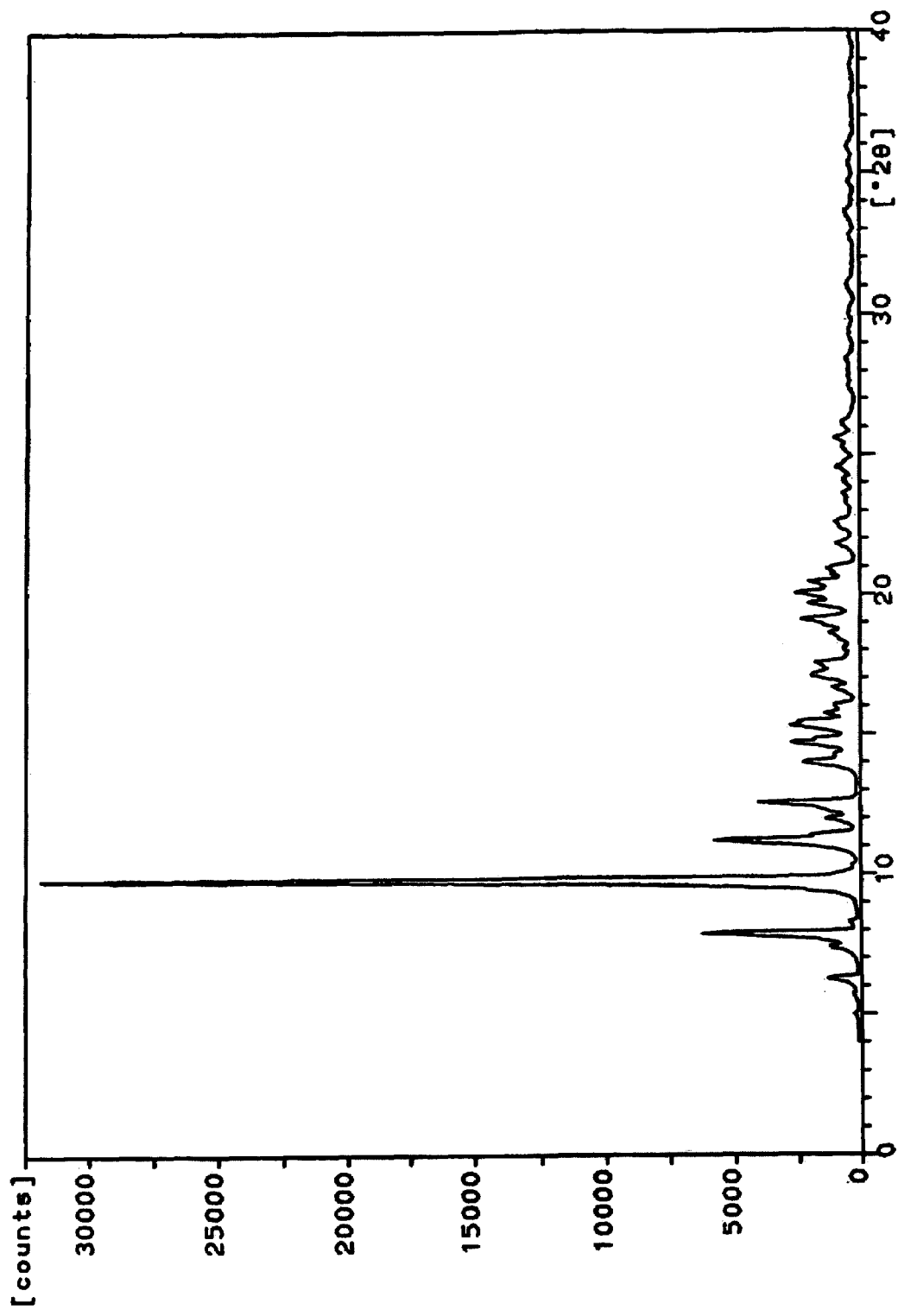
FIG. 1 shows the XRD graph of azithromycin monohydrate isopropanol clathrate

The final solid of azithromycin monohydrate isopropanol clathrate have the following d-spacing values in powder XRD, 14.23, 12.02, 11.24, 10.41, 9.03, 7.90, 7.38, 7.07, 6.34, 6.02, 5.79, 5.63, 5.53, 5.33, 5.18, 5.07, 4.76, 4.64, 4.51, 4.43, 4.25, 4.07, 3.93, 3.82, 3.77, 3.69, 3.62, 3.48, 3.41, 3.25, 3.19, 3.14, 2.87, 2.73 (FIG. 1).

Figure 2:
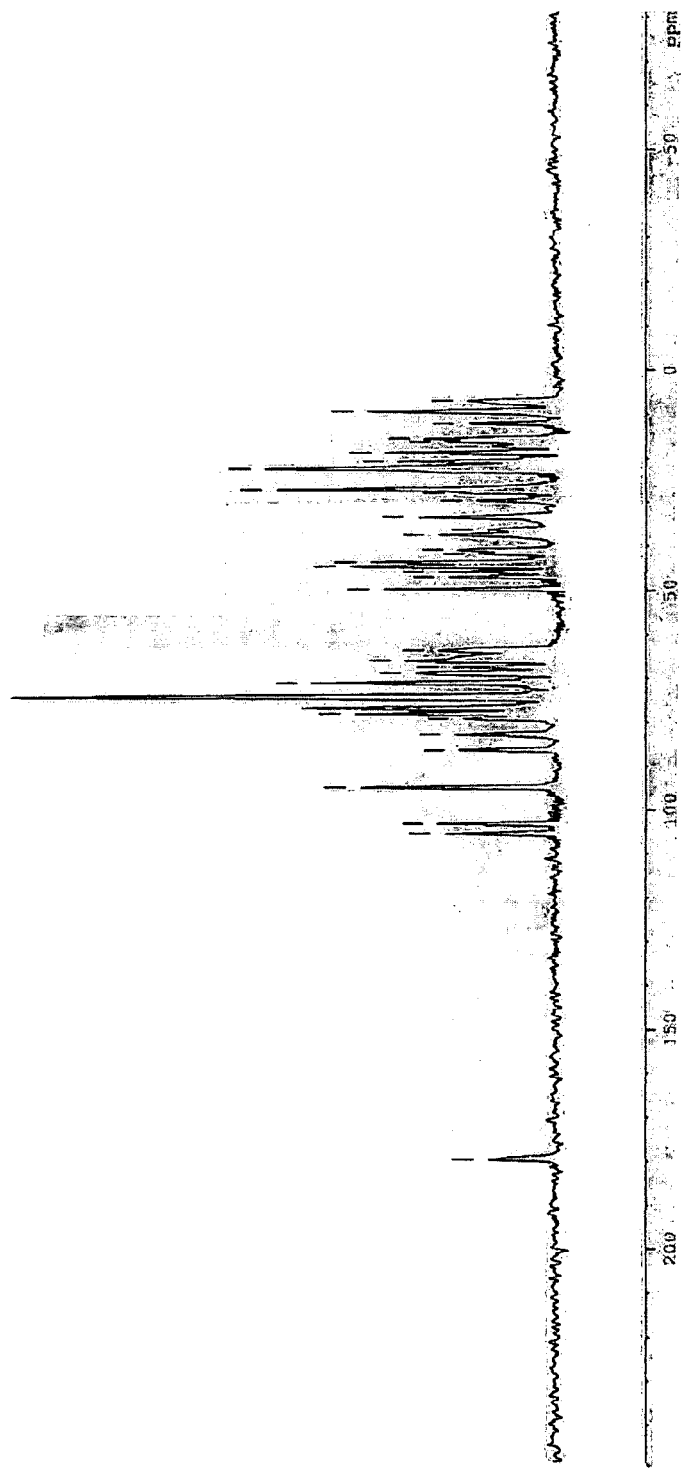
FIG. 2 shows the solid state NMR of azithromycin monohydrate isopropanol clathrate

The final solid of azithromycin monohydrate isopropanol clathrate have the solid state $^{13}$C NMR spectra having chemical shift in parts per million (ppm) at 179.39, 105.32, 103.06, 94.83, 86.26, 82.73, 79.13, 77.98, 76.69, 74.03, 70.98, 68.57, 67.34, 65.9, 63.49, 49.67, 46.87, 45.72, 44.5, 43.52, 41.63, 40.79, 37.3, 36.23, 33.35, 29.57, 27.84, 27.01, 22.29, 20.57, 18.64, 17.17, 16.11, 15.39, 11.99, 9.26, 6.89 (FIG. 2).

The water content of azithromycin monohydrate isopropanol clathrate was measured by Karl-Fischer method and its isopropanol content was determined by gas chromatography.

The invention will be more fully understood by the following examples, which illustrate the present invention but are not to be considered limiting to the scope of the invention.

EXAMPLE 1

Azaerythromycin 100 g (96.0%) is suspended in Isopropanol (300 ml) and the temperature is raised to 60–75° C. Methylating solution (23 ml formic acid (Assay=99%) and 23 ml formaldehyde 35%) are added over a period of 4–5 hours. The mixture is stirred for 12 hrs and then cooled to 40° C. The sodium hydroxide solution (25% w/v, 60–70 ml) is added in the reaction mixture and stirred for 20 minutes. Aqueous layer is separated and extracted with 75 ml isopropanol. Combined organic layer (Isopropanol) is distilled out up to foamy materials. Isopropanol (300 ml) is added and the reaction mass is heated to 45–50° C. Combine organic layer is clarified by filtration. To the filtered isopropanol solution, water (450 ml) is added to precipitate azithromycin monohydrate isopropanol clathrate. The mass is stirred for 6 hrs at 25 to 30° C. The resulting product is filtered and washed with 50:50 mixture of isopropanol-water. The product is dried under vacuum (1 to 10 mm Hg) at 25–50° C. temp for 2–10 hrs. Yield 89.0 gms (89%)
Isopropanol: 3.26%.
Water: 2.91%.

EXAMPLE 2

Azaerythromycin 100 g (96.0%) is suspended in Isopropanol (300 ml) and the temperature is raised to 60–65° C. Methylating solution (23.0 ml formic acid (Assay=99%) and 23 ml formaldehyde 35%) are added over a period of 4–5 hours. The mixture is stirred for 12 hrs and then the mass is cooled to 40° C. The sodium hydroxide solution (25% w/v, 60–70 ml) is added in the reaction mixture and stirred for 20 minutes. Aqueous layer is separated and extracted with 75 ml isopropanol. Combined organic layer (Isopropanol) is clarified by filtration. Water (570 ml) is added in 15–30 minutes and the reaction mass is stirred for 6–12 hrs at 25 to 30° C. temp. The resulting product is filtered and washed with 50:50 mixture of isopropanol-water. The product is dried under vacuum at 45–50° C. temp under reduced pressure. The product is dried under vacuum (1 to 10 mm Hg) at 25–50° C. temp for 2–10 hrs. Yield 94 gms (94%)
Isopropanol: 3.19%
Water: 2.5%

EXAMPLE 3

Azaerythromycin 100 g (89.0% purity) is suspended in Isopropanol (300 ml) at temperature of 25–30° C. To this solution formic acid (16.6 gms, 2.654 mole) and Paraformaldehyde (10.0 gms, 2.45 mole) are added and the temperature is raised up to 65–70° C. The mixture is stirred for 3–6 hrs and the mass is cooled to 40° C. The mixture is stirred for 12 hrs and cooled to 40° C. The sodium hydroxide solution (25% w/v, 60–70 ml) is added in the reaction mixture and stirred for 20 minutes. Aqueous layer is separated and extracted with 50 ml isopropanol. Combine organic layer (Isopropanol) is clarified by filtration and distilled isopropanol up to foamy materials., Isopropanol (300 ml) is added and the reaction mass is heated to 45–50° C. Combine organic layer is clarified by filtration. To the filtered isopropanol solution, water (400 ml) is added to precipitate azithromycin monohydrate isopropanol clathrate. The mass is then stirred for 6–12 hrs at 25 to 30° C. The resulting product is filtered and washed with 50:50 mixture of isopropanol-water. The product is dried under vacuum (1 to 10 mm Hg) at 25–50° C. temp for 2–10 hrs. Yield 70.0 gms (70%)
Isopropanol: 3.36%
Water: 2.04%

EXAMPLE 4

Azaerythromycin 100 g (purity=89%) is suspended in isopropanol (300 ml) at temperature of 25–35° C. To this solution formic acid (16.6 gms, 2.65 mole) and Paraformaldehyde (10.0 gms, 2.45 mole) are added and the temperature of reaction mass is raised to 65–70° C. The mixture is stirred for 3–6 hrs and cooled to 40° C. The sodium hydroxide solution (25% w/v, 60–70 ml) is added in the reaction mixture and stirred for 20 minutes. Aqueous layer is separated and extracted with 50 ml isopropanol. Combine organic layer (Isopropanol) is clarified by filtration. To the filtered isopropanol solution, water (400 ml) is added to precipitate azithromycin monohydrate isopropanol clathrate. The mass is then stirred for 6–12 hrs at 25 to 30° C. The resulting product is filtered and washed with 50:50 mixture of isopropanol-water. The product is dried under vacuum (1 to 10 mm Hg) at 25–50° C. temp for 2–10 hrs. Yield 80 gms (80%)
Isopropanol: 3.14%
Water: 2.56%

EXAMPLE 5

100 gms of Azithromycin Monohydrate Isopropanol Clathrate is suspended in Isopropanol 300 ml. The mixture is heated at 50 to 55° C. temp or dissolves the solid completely. In the reaction mixture water (450 ml) is added at the period of 15 to 30 minutes and stirred at six hrs at 20 to 30° C. The resulting product is filtered and washed with (50:50) IPA: water mixture. The product is dried under vacuum (1 mm to 10 mm Hg) at 25–50° C. temp.
Yield 89.0 gms (89%).
IPA=3.35%
Water=2.10%.

We claim:

1. A process for the preparation of azithromycin monohydrate isopropanal calthrate (Formula II),

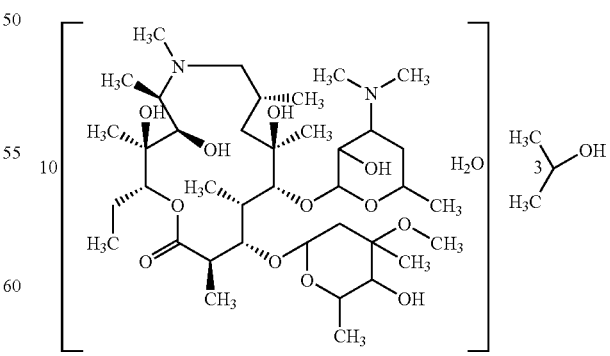

Formula II comprising the steps of:
(a) at least partial dissolution and/or suspension of 9-deoxo-9a-aza-9a homoerythromycin A in isopropanol to form a mixture;

(b) adding methylating solution to the said mixture;
(c) refluxing of heating said mixture to form a reaction mixture;
(d) adding alkaline solution to the reaction mixture to adjust pH from about 10 to about 11;
(e) isolating pure azithromycin monohydrate isopropanol clathrate.

2. Process as claimed in claim 1, wherein said step of isolating pure azithromycin monohydrate isopropanol clathrate comprises the steps of:
   (a) separating the organic layer from said reaction mixture;
   (b) adding water to said reaction mixture to precipitate said azithromycin monohydrate isopropanol clathrate;
   (c) filtering out said azithromycin monohydrate isopropanol clathrate;
   (d) vacuum drying the said azithromycin monohydrate isopropanol clathrate.

3. The process as claimed in claim 1, wherein the said methylating solution is selected from formaldehyde, formic acid, paraformaldehyde and mixture thereof.

4. The process as claimed in claim 1, wherein the said alkaline solution is selected from the group consisting of sodium hydroxide solution, potassium hydroxide solution.

5. The process as claimed in claim 4, wherein the alkaline solution is sodium hydroxide solution.

6. The process as claimed in claim 2, wherein the said vacuum drying comprises drying said Azithromycin monohydrate isopropanol clathrate at 25–60° C. under 1 to 10 mm Hg vacuum.

7. The process as claimed in claim 2, comprising filtering the reaction mixture after step (a).

8. The process as claimed in claim 2, wherein the product obtained in step (c) is washed with isopropanol and water mixture.

9. The process as claimed in claim 1, wherein the said refluxing or heating is carried out for 2–10 hrs at 40–90° C.

10. A process as claimed in claim 1, wherein the final solid of azithromycin monohydrate isopropanol clathrate have the following d-spacing values in powder XRD, 14.23, 12.02, 11.24, 10.41, 9.03, 7.90, 7.38, 7.07, 6.34, 6.02, 5.79, 5.63, 5.53, 5.33, 5.18, 5.07, 4.76, 4.64, 4.51, 4.43, 4.25, 4.07, 3.93, 3.82, 3.77, 3.69, 3.62, 3.48, 3.41, 3.25, 3.19, 3.14, 2.87, 2.73.

11. A process as claimed in claim 1, wherein the final solid of azithromycin monohydrate isopropanol clathrate have the solid state $^{13}$C NMR spectra having chemical shift in parts per million (ppm) at 179.39, 105.32, 103.06, 94.83, 86.26, 82.73, 79.13, 77.98, 76.69, 74.03, 70.98, 68.57, 67.34, 65.9, 63.49, 49.67, 46.87, 45.72, 44.5, 43.52, 41.63, 40.79, 37.3, 36.23, 33.35, 29.57, 27.84, 27.01, 22.29, 20.57, 18.64, 17.17, 16.11, 15.39, 11.99, 9.26, 6.89.

* * * * *